(12) United States Patent
Wang et al.

(10) Patent No.: US 12,133,512 B2
(45) Date of Patent: Nov. 5, 2024

(54) **ARTIFICIAL PROPAGATION METHOD OF *SINOCYCLOCHEILUS RHINOCEROUS***

(71) Applicant: Kunming Institute of Zoology, Chinese Academy of Sciences, Kunming (CN)

(72) Inventors: Xiao'ai Wang, Kunming (CN); Xiaofu Pan, Kunming (CN); Yuanwei Zhang, Kunming (CN); Junxing Yang, Kunming (CN); Bolin Lu, Kunming (CN)

(73) Assignee: Kunming Institute of Zoology, Chinese Academy of Sciences, Kunming (CN)

( * ) Notice: Subject to any disclaimer, the term of this patent is extended or adjusted under 35 U.S.C. 154(b) by 925 days.

(21) Appl. No.: 17/164,143

(22) Filed: Feb. 1, 2021

(65) Prior Publication Data
US 2022/0175507 A1   Jun. 9, 2022

(30) Foreign Application Priority Data
Dec. 4, 2020  (CN) .......................... 202011410487.2

(51) Int. Cl.
| | | |
|---|---|---|
| *A61D 19/02* | (2006.01) | |
| *A01K 61/10* | (2017.01) | |
| *A01K 61/17* | (2017.01) | |
| *A61L 2/00* | (2006.01) | |
| *A61L 101/02* | (2006.01) | |
| *C12N 5/073* | (2010.01) | |

(52) U.S. Cl.
CPC .............. *A01K 61/10* (2017.01); *A01K 61/17* (2017.01); *A61D 19/021* (2013.01); *C12N 5/0604* (2013.01)

(58) Field of Classification Search
CPC ........ A01K 61/00; A01K 61/80; A01K 61/10; A61D 19/00; A61D 19/021; A61L 2/0088; A61L 2101/02; C12N 5/0604
USPC .................. 119/218, 215, 217, 230
See application file for complete search history.

(56) References Cited

U.S. PATENT DOCUMENTS

| | | | | |
|---|---|---|---|---|
| 3,916,832 A | * | 11/1975 | Sweeney ................ | A01K 61/10 |
| | | | | 119/212 |
| 5,048,458 A | * | 9/1991 | Ebner .................... | A01K 61/17 |
| | | | | 119/217 |
| 5,660,142 A | * | 8/1997 | Van Rijn ................ | A01K 63/04 |
| | | | | 119/228 |
| 6,463,882 B1 | * | 10/2002 | Harris, Jr. ............. | A23K 50/80 |
| | | | | 119/230 |
| 6,564,747 B2 | * | 5/2003 | Harris, Jr. ............. | A01K 61/00 |
| | | | | 435/375 |
| 8,651,058 B1 | * | 2/2014 | Pierce ................... | A01G 31/00 |
| | | | | 119/215 |
| 11,547,097 B2 | * | 1/2023 | Zhang ................... | A01K 61/17 |
| 2011/0315086 A1 | * | 12/2011 | Kim ..................... | A01K 63/065 |
| | | | | 119/225 |
| 2022/0174915 A1 | * | 6/2022 | Zhang ................... | A01K 61/17 |

FOREIGN PATENT DOCUMENTS

| | | | | | |
|---|---|---|---|---|---|
| CN | 105409845 A | * | 3/2016 | ............. | A01K 61/00 |
| CN | 107372230 A | * | 11/2017 | | |
| CN | 110741983 A | * | 2/2020 | | |
| CN | 110741985 A | * | 2/2020 | | |

* cited by examiner

*Primary Examiner* — Tien Q Dinh
*Assistant Examiner* — Kevin M Dennis
(74) *Attorney, Agent, or Firm* — Thomas | Horstemeyer, LLP

(57) ABSTRACT

An artificial propagation method of *Sinocyclocheilus rhinocerous*, comprising placing female and male parent fish in a sterilized culture container in which a black cave simulant is placed in advance, strictly controlling the environmental parameters of the parent fish culture. The method realizes natural spawning and sperm production of *S. rhinocerous* under artificial conditions without using oxytocin. There is no oxytocin used in the artificial propagation, thus not only obtaining a higher fertilization rate and incubating rate, but also reducing the aquaculture cost. The operation is simpler and faster. At the same time, different feeds are fed in different growth stages according to the different growth characteristics of each stage of *S. rhinocerous* fry, thereby increasing the survival rate and reducing the deformity rate of fries. Therefore, the method provided by the present disclosure realizes efficient artificial propagation method of *S. rhinocerous*.

18 Claims, No Drawings ated with fertilized eggs on the palmsheet adhered with ferti-

ARTIFICIAL PROPAGATION METHOD OF SINOCYCLOCHEILUS RHINOCEROUS

CROSS-REFERENCE TO RELATED APPLICATIONS

This application claims the priority of Chinese Patent Application No. 202011410487.2, entitled "Artificial Propagation Method Of *Sinocyclocheilus Rhinocerous*" filed with China National Intellectual Property Administration on Dec. 4, 2020, which is incorporated herein by reference in its entirety.

TECHNICAL FIELD

The present disclosure belongs to the technical field of aquaculture, especially relating to an artificial propagation method of *Sinocyclocheilus rhinocerous*.

BACKGROUND ART

*Sinocyclocheilus*, belonging to Cyprinidae of Cypriniformes, is an endemic Chinese fish confined to the southwest kaster region of China. This genus is the largest genus of Cyprinidae fishes in China, with more than 50 different species, and is also a representative group of cave creatures in our country, with about 50% of the species being cave fish. These cave fishes have highly specialized cave characteristics, such as eye degradation, skin albinism, scale disappearance, etc. They live in the depths of light-free cavities for a long time, which is an excellent material for studying the survival adaptation of organisms in extreme environments, and also an ideal model animal for studying human diseases such as oculopathy, albinism, metabolic disease, etc. Compared with the surface species, such as *Sinocyclocheilus grahami* and *Sinocyclocheilus grahami tingi*, the cave species are much more difficult to domesticate and artificially propagate, and there have been no successful cases of artificial reproduction so far, thus, severely limiting the development of the above-mentioned studies on human diseases.

*Sinocyclocheilus rhinocerous* (*Sinocyclocheilus rhinocerous* Li et Tao, 1994) is a new cave species of the *Sinocyclocheilus* discovered in 1994. At present, the known distribution spot of *S. rhinocerous* is the underground river in the Huancheng township, Luoping County, Yunnan Province, which belongs to the Nanpanjiang water system. The population of *S. rhinocerous* is small and it is not easy to collect in the field. The study on it has only been in the description of classification features, the confirmation of the taxonomic status, the phylogenetic relationship and the whole genome study. Beginning in 2004, the Kunming Institute of Zoology, Chinese Academy of Sciences has been committed to the research on artificial reproduction of *S. rhinocerous*. After long-term domestication and parental fish culture, the artificial reproduction of *S. rhinocerous* was finally realized without using oxytocin, becoming the first cave fish to realize artificial reproduction, and the artificial reproduction of *S. rhinocerous* has created more possibilities for cave adaptation study of Chinese cave fishes. However, after literature search, there is no report about artificial propagation method of *S. rhinocerous*.

SUMMARY OF THE INVENTION

In view of this, the purpose of the present disclosure is to provide an artificial propagation method of *S. rhinocerous*, thus realizing the natural spawning and sperm production of *S. rhinocerous* under artificial conditions, and obtaining the high fertilization rate without using oxytocin.

The present disclosure provides an artificial propagation method of *S. rhinocerous*, comprising the following steps:

placing female and male parent fish in a sterilized culture container for parent fish culture, wherein black cave simulant is placed in the culture container in advance; the environmental parameters during parent fish culture are as follows: water temperature is in a range of 16-20° C., water flow velocity is in a range of 5-20 cm/s, the concentration of dissolved oxygen of water is in a range of 6.0-7.0 mg/L, and water pH is in a range of 6.8-7.2, keeping the water clean; keeping the culture environment dark and noiseless;

during the parent fish culture, feeding pellet feed twice a day, and the feeding amount is according to the feed coefficient of 3%-4%, the pellet feed is a mixture of mash feed containing 40%-50% crude protein, earthworm, shrimp, vitamin D3 calcium tablets, multi-vitamin tablets and water, with a mass ratio of 250-280:80-100:10-20:10-20:8-20:300;

collecting sperm and eggs for artificial inseminating after the gonads of female and male parent fish mature, rinsing the sperm-egg mixture with normal saline with osmotic pressure of 280-320 mOsm/L and temperature of 18-20° C. for 3-4 times, then splashing the sperm-egg mixture on the sterilized palmsheet, and incubating the palmsheet adhered with fertilized eggs in the incubating pond for 7-8 days, breeding the incubated fries to obtain the adult fish of *S. rhinocerous*.

In some embodiments, the environmental parameters of parent fish culture are rhythmically regulated (the "rhythmically regulated" means regulating according to season, climate, etc., or regulating according to specific climatic parameters, such as temperature, humidity, etc.):

in Stage 1 (4 months, such as January to April in China): water temperature is in a range of 16-20° C., water flow velocity is in a range of 10-20 cm/s, the concentration of dissolved oxygen of water is in a range of 6.0-7.0 mg/L, and water pH is in a range of 6.8-7.0;

in Stage 2 (4 months, such as May to August in China): water temperature is in a range of 18-20° C., water flow velocity is in a range of 5-15 cm/s, the concentration of dissolved oxygen of water is in a range of 6.0-6.5 mg/L, and water pH is in a range of 6.8-7.2;

in Stage 3 (4 months, such as September to December in China): water temperature is in a range of 16-18° C., water flow velocity is in a range of 5-15 cm/s, the concentration of dissolved oxygen of water is in a range of 6.0-7.0 mg/L, and water pH is in a range of 6.8-7.2.

In some embodiments, the type of pellet feed is rhythmically regulated:

feeding feed SRF1 in Stage 1, wherein the feed SRF1 is a mixture of mash feed containing 50% crude protein, earthworm, shrimp, vitamin D3 calcium tablets, multi-vitamin tablets and water, with a mass ratio of 250:100:20:10:8:300;

feeding feed SRF2 in Stage 2, wherein the feed SRF2 is a mixture of mash feed containing 40% crude protein, earthworm, shrimp, vitamin D3 calcium tablets, multi-vitamin tablets and water, with a mass ratio of 280:80:10:20:10:300;

feeding feed SRF3 in Stage 3, wherein the feed SRF3 is a mixture of mash feed containing 45% crude protein, earthworm, shrimp, vitamin D3 calcium tablets, multi-vitamin tablets and water, with a mass ratio of 250:100:10:20:20:300.

In some embodiments, the environmental conditions for the incubating are as follows:

water level is 1.2 m, water surface is in a range of 40-80 cm above fish eggs, no direct light source, water temperature is in a range of 18-20° C., water pH is in a range of 6.8-7.5, the concentration of dissolved oxygen of water is in a range of 7.0-8.0 mg/L.

In some embodiments, the fertilized eggs are sterilized during incubating;

wherein the sterilizing comprising: sterilizing the fertilized eggs in 80-120 ppm potassium permanganate solution for 15-25 min, and sterilizing for 4 consecutive days.

In some embodiments, the water quality is regulated by adding nitrifying bacteria in an amount of 15-17 $g/m^2$ every day during the feeding period.

In some embodiments, the fries are fed 7 days after breaking egg membrane, and feeding the feed in stages during the feeding period.

In some embodiments, feeding pulpous feed SRF4 from the 1st day to the 7th day of feeding, 4 times per day with the feeding amount of 8-10 $mL/m^2$, wherein the pulpous feed SRF4 is a mixture of boiled egg yolk, earthworm, shrimp, multi-vitamin tablets and water, with amass ratio of 300:20:20:10:750;

feeding feed SRF5 and rotifer from the 8th day to the 20th day of feeding, 3 times per day, the feeding amount of feed SRF5 each time is 10-15 $mL/m^2$; the feeding amount of rotifer each time is 1.5 million/$m^2$, wherein the feed SRF5 is a mixture of boiled egg yolk, earthworm, shrimp, freshly ground soybean milk, multi-vitamin tablets and water, with a mass ratio of 250:20:20:250:10:750;

feeding feed SRF6 from the 21st day to the 60th day of feeding, twice a day with the feeding amount of 10-12 $g/m^2$, wherein the feed SRF6 is a mixture of freshly ground soybean milk, earthworm, shrimp, mash feed containing 40% crude protein, vitamin D3 calcium tablets, multi-vitamin tablets and water, with a mass ratio of 250:10:10:250:10:10:750;

after feeding for 60 days, feeding pellet feed twice a day, the feeding amount each time is according to the feed coefficient of 3%-4%.

The artificial propagation method of S. rhinocerous provided by the present disclosure, comprising placing black cave simulant in the culture container in advance; strictly controlling the environmental parameters during the parent fish culture, improving the parent fish culture process, has fundamentally solved the dual problems of stress and adaptation of cave fish from the wild cave environment to the artificial simulated environment and the reproductive dysfunction of cave fish under artificial conditions. At the same time, the female and male parent fish can realize natural spawning and sperm production under artificial conditions without using oxytocin, and obtaining a higher fertilization rate and incubating rate. There is no oxytocin used in the artificial propagation, thus not only reducing the damage to the parent fish of S. rhinocerous, but also reducing the aquaculture cost. The operation is simpler and faster.

Furthermore, in the present disclosure, the rhythmic adjustment of environmental parameters and feeding method during the parent fish culture is specifically defined, which makes the living environment of the parent fish closer to the natural environment, and ensure the normal development and reproductive performance of spermatogenesis and oviposition of parent fish.

Furthermore, in the present disclosure, the incubation method is specifically defined, and the setting of incubation environment parameters and the limitation of the disinfection steps during incubating are beneficial to further increase the incubation rate and speed.

Furthermore, in the present disclosure, the staged feeding of fry is specifically defined, and according to the different growth characteristics of each stage of S. rhinocerous fry, the feed formula and feeding amount of different growth stages are set, which not only improves the survival rate of fry but also reduces the teratological rate of fry.

DETAILED DESCRIPTION OF THE EMBODIMENTS

The present disclosure provides an artificial propagation method of *Sinocyclocheilus rhinocerous*, comprising the following steps:

placing female and male parent fish in a sterilized culture container for parent fish culture, wherein black cave simulant is placed in the culture container in advance; the environmental parameters during parent fish culture are as follows: water temperature is in a range of 16-20° C., water flow velocity is in a range of 5-20 cm/s, the concentration of dissolved oxygen of water is in a range of 6.0-7.0 mg/L, and water pH is in a range of 6.8-7.2, keeping the water clean; keeping the culture environment dark and noiseless;

during the parent fish culture, feeding pellet feed twice a day, and the feeding amount is according to the feed coefficient of 3%-4%, and the pellet feed is a mixture of mash feed containing 40%-50% crude protein, earthworm, shrimp, vitamin D3 calcium tablets, multi-vitamin tablets and water, with a mass ratio of 250-280:80-100:10-20:10-20:8-20:300;

collecting sperm and eggs for artificial inseminating after the gonads of female and male parent fish mature, rinsing the sperm-egg mixture with normal saline with osmotic pressure of 280-320 mOsm/L and temperature of 18-20° C. for 3-4 times, then splashing the sperm-egg mixture on the sterilized palmsheet, and incubating the palmsheet adhered with fertilized eggs in the incubating pond for 7-8 days, breeding the incubated fries to obtain the adult fish of S. rhinocerous.

In the present disclosure, black cave simulant is placed in the culture container in advance. In some embodiments, the black cave simulant is a black tubular member, so as to satisfy the cave survival habits of parent fish. In the present disclosure, there is no particular limitation on the types of black tubular member, the types well known in the art will do, such as a black PVC pipe. In some embodiments, the inner diameter of the black tubular member is 15 cm, and the length is preferably 30 cm. In some embodiments, the culture cylinder and the black cave simulant are disinfected first, and then the parent fish culture is carried out. In the present disclosure, there is no particular limitation on the disinfection method, the disinfection method well known in the art will do. In some embodiments, the cultivation container is a cultivation cylinder or a cultivation pond, etc. In some embodiments, the specification of the cultivation cylinder is 1 m×0.8 m×1 m, and 1 to 2 black cave simulants are preferably placed in each cultivation cylinder.

In some embodiments, the environmental parameters of parent fish culture are rhythmically regulated: in Stage 1 (4 months, such as January to April in China), water temperature is in a range of 16-20° C., water flow velocity is in a range of 10-20 cm/s, the concentration of dissolved oxygen of water is in a range of 6.0-7.0 mg/L, and water pH is in a range of 6.8-7.0; in Stage 2 (4 months, such as May to August in China), water temperature is in a range of 18-20° C., water flow velocity is in a range of 5-15 cm/s, the concentration of dissolved oxygen of water is in a range of 6.0-6.5 mg/L, and water pH is in a range of 6.8-7.2; in Stage 3 (4 months, such as September to December in China), water temperature is in a range of 16-18° C., water flow velocity is in a range of 5-15 cm/s, the concentration of dissolved oxygen of water is in a range of 6.0-7.0 mg/L, and water pH is in a range of 6.8-7.2. The 3 periods are set mainly based on the actual demands of different stages, Stage 1 (such as January to April in China) is the breeding period, Stage 2 (such as May to August in China) is postpartum recovery period, Stage 3 (such as September to December in China) is the gonadal maturity period, which is the pregnant period. It has been experimentally demonstrated that parent fish culture above or below these environmental parameters results in poor gonadal development of parent fish or poor sperm and egg quality. Food residues, feces, etc. need to be removed every day to keep the water body clean. The filtration device of the incubation container is cleaned every day. The cultivation container is kept dark throughout the year, and there is no noise around it, so as to reduce the stress of parent fish to the environment, make it adapt to the artificial cultivation environment, and avoid reproductive dysfunction.

In some embodiments, the type of pellet feed is rhythmically regulated: feeding feed SRF1 in Stage 1, wherein the feed SRF1 is a mixture of mash feed containing 50% crude protein, earthworm, shrimp, vitamin D3 calcium tablets, multi-vitamin tablets and water, with amass ratio of 250:100:20:10:8:300;

feeding feed SRF2 in Stage 2, wherein the feed SRF2 is a mixture of mash feed containing 40% crude protein, earthworm, shrimp, vitamin D3 calcium tablets, multi-vitamin tablets and water, with a mass ratio of 280:80:10:20:10:300;

feeding feed SRF3 in Stage 3, wherein the feed SRF3 is a mixture of mash feed containing 45% crude protein, earthworm, shrimp, vitamin D3 calcium tablets, multi-vitamin tablets and water, with a mass ratio of 250:100:10:20:20:300. In the present disclosure, artificial compound feed is creatively prepared suitable for different parent fish growth stages. Compared with other kinds of conventional raw material mixture, the feed SRF1~SRF3 provided by the disclosure can promote the rapid growth and development of parent fish and natural spawning and sperm production.

Sperm and eggs are collected for artificial inseminating after the gonads of female and male parent fish mature.

In some embodiments, the selection criteria for the female and male parent fish after the gonads of female and male parent fish mature is as follows: fertilizing the female and male parent fish with good gonadal development and no disease. During the propagative period, neither female nor male parent fish has pearl stars, and there is no obvious roughness when touched by hand; in morphology, parent fish is round due to the swelling of the eggs or sperm abdomen, and sperm or eggs will flow out when the abdomen is lightly pressed. In the present disclosure, there is no particular limitation on the method for collecting eggs and sperm, the collecting method well known in the art will do. In some embodiments, the artificial inseminating preferably gently stirs the mixture of eggs and sperm with feathers clockwise for 30 s. After artificial inseminating, rinsing the sperm-egg mixture with normal saline with osmotic pressure of 280-320 mOsm/L and temperature of 18-20° C. for 3 times, which is conducive to reduce the mold infection rate on fertilized eggs. Splashing the sperm-egg mixture evenly on the sterilized palmsheet after artificial inseminating, so that the fertilized egg can be fixed on the palmsheet in preparation for subsequent incubating.

In some embodiments, the environmental conditions for the incubating are as follows: water level of cultivation pond is 1.2 m, water surface is in a range of 40-80 cm above fish eggs, no direct light source, water temperature is in a range of 18-20° C., water pH is in a range of 6.8-7.5, the concentration of dissolved oxygen of water is in a range of 7.0-8.0 mg/L. In some embodiments, the fertilized eggs are sterilized during incubating; the sterilizing comprising: sterilizing the fertilized eggs in 80-120 ppm potassium permanganate solution for 15-5 min, and sterilizing for 4 consecutive days, the fry incubates on the 5th day and the incubation ends on the 8th day. The concentration of the potassium permanganate solution is more preferably 100 ppm, and the disinfecting time is preferably 20 min. The incubating conditions are beneficial for rapid incubating of fertilized eggs into fries.

In some embodiments, the water quality is regulated by adding nitrifying bacteria in an amount of 15-17 $g/m^2$ every day during the feeding period. The nitrifying bacteria is purchased through conventional commercial routes. In some embodiments, the adding amount of nitrifying bacteria is 16 $g/m^2$.

In some embodiments, fries are fed 7 days after breaking egg membrane, and feeding the feed in stages during the feeding period. In some embodiments, feeding pulpous feed SRF4 from the 1st day to the 7th day of feeding, 4 times per day with the feeding amount of 8-10 $mL/m^2$, wherein the pulpous feed SRF4 is a mixture of boiled egg yolk, earthworm, shrimp, multi-vitamin tablets and water, with a mass ratio of 300:20:20:10:750; feeding feed SRF5 and rotifer from the 8th day to the 20th day of feeding, 3 times per day, the feeding amount of feed SRF5 each time is 10-15 $mL/m^2$; the feeding amount of rotifer each time is 1.5 million/$m^2$, wherein the feed SRF5 is a mixture of boiled egg yolk, earthworm, shrimp, freshly ground soybean milk, multi-vitamin tablets and water, with a mass ratio of 250:20:20:250:10:750. After feeding for 8-20 days, the fry starts to absorb exogenous nutrients and it is very important for the opening feed. If too early, the fry does not need to eat, the feed sprinkles in the water and pollutes the water; if too late, without suitable feed, all the fries will be died. Feeding feed SRF6 from the 21st day to the 60th day of feeding, twice a day with the feeding amount of 10-12 $g/m^2$, wherein the feed SRF6 is a mixture of freshly ground soybean milk, earthworm, shrimp, mash feed containing 40% crude protein, vitamin D3 calcium tablets, multi-vitamin tablets and water, with a mass ratio of 250:10:10:250:10:10:750; after feeding for 60 days, feeding pellet feed twice a day, the feeding amount each time is according to the feed coefficient of 3%-4%. In the present disclosure, there is no particular limitation on the source of the raw materials of the feed, the raw materials well known in the art will do.

The artificial propagation method of *S. rhinocerous* provided by the present disclosure will be described clearly and completely in combination with the examples in the disclosure, but they should not be understood as limiting the protection scope of the present disclosure.

Example 1

1. Building a Breeding System

Parent fish cultivation cylinder was established, the specification of the cultivation cylinder was 1 m×0.8 m×1 m (length×width×height), and the cultivation container was kept dark throughout the year, and there was no noise around it, the parameters of water temperature, water flow intensity and water quality in the cultivation cylinder could be rhythmically regulated according to the requirements, that is, in Stage 1 (from January to April), the temperature was controlled at 18° C., the water flow rate was controlled at 15 cm/s, the concentration of dissolved oxygen of water was controlled at 6.5 mg/L, and the water pH was controlled at 6.9; in Stage 2 (from May to August), the temperature was controlled at 19° C., the water flow rate was controlled at 10 cm/s, the concentration of dissolved oxygen of water was controlled at 6.3 mg/L and the water pH was controlled at 7.0; in Stage 3 (from September to December), the temperature was controlled at 17° C., the water flow rate was controlled at 10 cm/s, the concentration of dissolved oxygen of water was controlled at 6.5 mg/L, and the water pH was controlled at 7.0. The filtration device of the incubation container was cleaned every day to keep the water quality clean.

2. Preparation of Feed

SRF1 feed: mash feed containing 50% crude protein, earthworm, shrimp, vitamin D3 calcium tablets, multi-vitamin tablets and water; mash feed containing 50% crude protein:earthworm:shrimp:vitamin D3 calcium tablets:multi-vitamin tablets:water=250:100:20:10:8:300 (mass ratio).

SRF2 feed: mash feed containing 40% crude protein, earthworm, shrimp, vitamin D3 calcium tablets, multi-vitamin tablets and water; mash feed containing 40% crude protein:earthworm:shrimp:vitamin D3 calcium tablets:multi-vitamin tablets:water=280:80:10:20:10:300 (mass ratio).

SRF3 feed: mash feed containing 45% crude protein, earthworm, shrimp, vitamin D3 calcium tablets, multi-vitamin tablets and water; mash feed containing 45% crude protein:earthworm:shrimp:vitamin D3 calcium tablets:multi-vitamin tablets:water=250:100:10:20:20:300 (mass ratio).

SRF4 feed: boiled egg yolk, earthworm, shrimp, multi-vitamin tablets and water; boiled egg yolk:earthworm:shrimp:multi-vitamin tablets:water=300:20:20:10:750 (mass ratio).

SRF5 feed: boiled egg yolk, earthworm, shrimp, freshly ground soybean milk, multi-vitamin tablets and water; boiled egg yolk:earthworm:shrimp: freshly ground soybean milk:multi-vitamin tablets:water=250:20:20:250:10:750 (mass ratio).

SRF6 feed: freshly ground soybean milk, earthworm, shrimp, mash feed containing 40% crude protein, vitamin D3 calcium tablets, multi-vitamin tablets and water; freshly ground soybean milk:earthworm:shrimp:mash feed containing 40% crude protein:vitamin D3 calcium tablets:multi-vitamin tablets:water=250:10:10:250:10:10:750 (mass ratio).

3. Source of Parent Fish

The parent fish was collected in a cave next to the Chaishitan reservoir, belongs to the Nanpanjiang water system, in Yiliang County, Yunnan Province in March 2019, all of which were caught by using ground cages with a total of 15 fish. Parent fish were packed into plastic fry bags with a length of 80 cm and a width of 50 cm, which were flushed with oxygen and brought back to the breeding base.

4. Cultivation of Parent Fish

The parent fish collected in the field was placed in a sterilized cultivation cylinder, and a black PVC tube with a length of 30 cm and a diameter of 15 cm was placed in the cultivation cylinder; the water temperature was 18° C., water flow velocity was 12 cm/s, the concentration of dissolved oxygen of water was 6.5 mg/L, and water pH was 7.0. SRF1 feed was fed at 10:00 and 16:00 every day. After 1 week of domesticating, 2 parent fish died in total.

During the propagative period, neither female nor male parent fish had pearl stars, and there was no obvious roughness when touched by hand; in morphology, female parent fish abdomen was enlarged and round due to pregnancy, and eggs were flow out when the abdomen was lightly pressed.

5. Artificial Insemination

In the breeding period, the male and female parent fish with good gonad development and disease-free were selected for artificial inseminating. The eggs and sperm of the parent fish were gently squeezed into a pre-prepared container, and immediately stirred gently with chicken feathers for 30 s. Then, the sperm-egg mixture was rinsed gently with water with osmotic pressure of 280 mOsm/L and temperature of 19° C. After rinsing for 3 times, the sperm-egg mixture was evenly splashed on the sterilized and washed palmsheet.

6. Incubation of Fish Eggs

The palmsheet adhered with fertilized eggs were placed in a sterilized and washed incubating pond (5 m×4 m×1.5 m) with a water level of 1.2 m, water surface 60 cm above the eggs, which was covered with shading net to ensure that there was no direct light source, the water temperature was 19° C., the water pH was 7.2 and the concentration of dissolved oxygen of water was 7.5 mg/L; every day, the eggs were sterilized in 100 ppm potassium permanganate solution for 20 min for 4 consecutive days. The fries incubated on the 5th day, and the incubation ended on the 8th day.

7. Breeding of Fries

The fries were fed 7 days after breaking egg membrane, and the water quality was regulated by adding nutrifying bacteria at 16 g/m$^2$ every day. Different feeds were fed according to stages, wherein, in the fry rearing stage:

from the 1st to 7th day of the feeding period, pulpous SRF4 was fed 4 times per day, and the feeding amount was 9 mL/m$^2$;

from the 8th to 20th day, the feed SCF5 and rotifer were fed 3 times per day, and the feeding amount of rotifer was 1.5 million/m$^2$, the feeding amount of feed SCF5 was 10 mL/m$^2$;

from the 21st to 60th day, the feed SCF6 was fed with the feeding amount of 11 g/m$^2$;

after 60 days of feeding, the fries were fed with feed used for parent fish culture, and the feeding amount was according to the feed coefficient of 4%, and the feeding amount was consumed within 20 min, the adult of *S. rhinocerous* was obtained after feeding for 1 year.

Example 2

1. Building a Breeding System

Parent fish cultivation cylinder was established, the specification of the cultivation cylinder was 1 m×0.8 m×1 m (length×width×height), and the cultivation container was kept dark throughout the year, and there was no noise around it, the parameters of water temperature, water flow intensity and water quality in the cultivation cylinder could be rhythmically regulated according to the requirements, that is, in Stage 1 (from January to April), the temperature was controlled at 20° C., the water flow rate was controlled at 10 cm/s, the concentration of dissolved oxygen of water was controlled at 7.0 mg/L, and the water pH was controlled at 6.8; in Stage 2 (from May to August), the temperature was controlled at 20° C., the water flow rate was controlled at 5 cm/s, the concentration of dissolved oxygen of water was controlled at 6.5 mg/L and the water pH was controlled at 6.8; in Stage 3 (from September to December), the temperature was controlled at 18° C., the water flow rate was controlled at 5 cm/s, the concentration of dissolved oxygen of water was controlled at 7.0 mg/L, and the water pH was controlled at 6.8. The filtration device of the incubation container was cleaned every day to keep the water quality clean.

2. Preparation of Feed

SRF1 feed: mash feed containing 50% crude protein, earthworm, shrimp, vitamin D3 calcium tablets, multi-vitamin tablets and water; mash feed containing 50% crude protein: earthworm:shrimp:vitamin D3 calcium tablets: multi-vitamin tablets:water=250:100:20:10:8:300 (mass ratio).

SRF2 feed: mash feed containing 40% crude protein, earthworm, shrimp, vitamin D3 calcium tablets, multi-vitamin tablets and water; mash feed containing 40% crude protein: earthworm:shrimp:vitamin D3 calcium tablets: multi-vitamin tablets:water=280:80:10:20:10:300 (mass ratio).

SRF3 feed: mash feed containing 45% crude protein, earthworm, shrimp, vitamin D3 calcium tablets, multi-vitamin tablets and water; mash feed containing 45% crude protein: earthworm:shrimp:vitamin D3 calcium tablets: multi-vitamin tablets:water=250:100:10:20:20:300 (mass ratio).

SRF4 feed: boiled egg yolk, earthworm, shrimp, multi-vitamin tablets and water; boiled egg yolk:earthworm: shrimp:multi-vitamin tablets:water=300:20:20:10:750 (mass ratio).

SRF5 feed: boiled egg yolk, earthworm, shrimp, freshly ground soybean milk, multi-vitamin tablets and water; boiled egg yolk:earthworm:shrimp: freshly ground soybean milk:multi-vitamin tablets:water=250:20:20:250:10:750 (mass ratio).

SRF6 feed: freshly ground soybean milk, earthworm, shrimp, mash feed containing 40% crude protein, vitamin D3 calcium tablets, multi-vitamin tablets and water; freshly ground soybean milk:earthworm:shrimp:mash feed containing 40% crude protein:vitamin D3 calcium tablets:multi-vitamin tablets:water=250:10:10:250:10:10:750 (mass ratio).

3. Source of Parent Fish

The parent fish was collected in a cave next to the Chaishitan reservoir, belongs to the Nanpanjiang water system, in Yiliang County, Yunnan Province in March 2019, all of which were caught by using ground cages with a total of 15 fish. Parent fish were packed into plastic fry bags with a length of 80 cm and a width of 50 cm, which were flushed with oxygen and brought back to the breeding base.

4. Cultivation of Parent Fish

The parent fish collected in the field was placed in a sterilized cultivation cylinder, and a black PVC tube with a length of 30 cm and a diameter of 15 cm was placed in the cultivation cylinder; the water temperature was 20° C., water flow velocity was 10 cm/s, the concentration of dissolved oxygen of water was 7.0 mg/L, and water pH was 6.8. SRF1 feed was fed at 10:00 and 16:00 every day. After 1 week of domesticating, 2 parent fish died in total.

During the propagative period, neither female nor male parent fish had pearl stars, and there was no obvious roughness when touched by hand; in morphology, female parent fish abdomen was enlarged and round due to pregnancy, and eggs were flow out when the abdomen was lightly pressed.

5. Artificial Insemination

In the breeding period, the male and female parent fish with good gonad development and disease-free were selected for artificial inseminating. The eggs and sperm of the parent fish were gently squeezed into a pre-prepared container, and immediately stirred gently with chicken feathers for 30 s. Then, the sperm-egg mixture was rinsed gently with water with osmotic pressure of 320 mOsm/L and temperature of 20° C. After rinsing for 3 times, the sperm-egg mixture was evenly splashed on the sterilized and washed palmsheet.

6. Incubation of Fish Eggs

The palmsheet adhered with fertilized eggs were placed in a sterilized and washed incubating pond (5 m×4 m×1.5 m) with a water level of 1.2 m, water surface 80 cm above the eggs, which was covered with shading net to ensure that there was no direct light source, the water temperature was 18° C., water pH was 7.5 and the concentration of dissolved oxygen of water was 7.0 mg/L; every day, the eggs were sterilized in 100 ppm potassium permanganate solution for 20 min for 4 consecutive days. The fries incubated on the 5th day, and the incubation ended on the 8th day.

7. Breeding of Fries

The fries were fed 7 days after breaking egg membrane, and the water quality was regulated by adding nutrifying bacteria at 17 g/m$^2$ every day. Different feeds were fed according to stages, wherein, in the fry rearing stage:

from the 1st to 7th day of the feeding period, pulpous SRF4 was fed 4 times per day, and the feeding amount was 10 mL/m$^2$;

from the 8th to 20th day, the feed SCF5 and rotifer were fed 3 times per day, and the feeding amount of rotifer was 1.5 million/m$^2$, the feeding amount of feed SCF5 was 15 mL/m$^2$;

from the 21st to 60th day, the feed SCF6 was fed with the feeding amount of 12 g/m$^2$;

after 60 days of feeding, the fries were fed with feed used for parent fish culture, and the feeding amount was according to the feed coefficient of 4%, and the feeding amount was consumed within 30 min, the adult of *S. rhinocerous* was obtained after feeding for 1 year.

Example 3

1. Building a Breeding System

Parent fish cultivation cylinder was established, the specification of the cultivation cylinder was 1 m×0.8 m×1 m (length×width×height), and the cultivation container was kept dark throughout the year, and there was no noise around it, the parameters of water temperature, water flow intensity and water quality in the cultivation cylinder could be rhythmically regulated according to the requirements, that is, in Stage 1 (from January to April), the temperature was controlled at 16° C., the water flow rate was controlled at 20 cm/s, the concentration of dissolved oxygen of water was controlled at 6.0 mg/L, and the water pH was controlled at 7.0; in Stage 2 (from May to August), the temperature was controlled at 18° C., the water flow rate was controlled at 15 cm/s, the concentration of dissolved oxygen of water was controlled at 6.0 mg/L and the water pH was controlled at 7.2; in Stage 3 (from September to December), the temperature was controlled at 16° C., the water flow rate was controlled at 15 cm/s, the concentration of dissolved oxygen of water was controlled at 6.0 mg/L, and the water pH was controlled at 7.2. The filtration device of the incubation container was cleaned every day to keep the water quality clean.

2. Preparation of Feed

SRF1 feed: mash feed containing 50% crude protein, earthworm, shrimp, vitamin D3 calcium tablets, multi-vitamin tablets and water; mash feed containing 50% crude protein: earthworm:shrimp:vitamin D3 calcium tablets: multi-vitamin tablets:water=250:100:20:10:8:300 (mass ratio).

SRF2 feed: mash feed containing 40% crude protein, earthworm, shrimp, vitamin D3 calcium tablets, multi-vitamin tablets and water; mash feed containing 40% crude protein: earthworm:shrimp:vitamin D3 calcium tablets: multi-vitamin tablets:water=280:80:10:20:10:300 (mass ratio).

SRF3 feed: mash feed containing 45% crude protein, earthworm, shrimp, vitamin D3 calcium tablets, multi-vitamin tablets and water; mash feed containing 45% crude protein: earthworm:shrimp:vitamin D3 calcium tablets: multi-vitamin tablets:water=250:100:10:20:20:300 (mass ratio).

SRF4 feed: boiled egg yolk, earthworm, shrimp, multi-vitamin tablets and water; boiled egg yolk:earthworm: shrimp:multi-vitamin tablets:water=300:20:20:10:750 (mass ratio).

SRF5 feed: boiled egg yolk, earthworm, shrimp, freshly ground soybean milk, multi-vitamin tablets and water; boiled egg yolk:earthworm:shrimp: freshly ground soybean milk:multi-vitamin tablets:water=250:20:20:250:10:750 (mass ratio).

SRF6 feed: freshly ground soybean milk, earthworm, shrimp, mash feed containing 40% crude protein, vitamin D3 calcium tablets, multi-vitamin tablets and water; freshly ground soybean milk:earthworm:shrimp:mash feed containing 40% crude protein:vitamin D3 calcium tablets:multi-vitamin tablets:water=250:10:10:250:10:10:750 (mass ratio).

3. Source of Parent Fish

The parent fish was collected in a cave next to the Chaishitan reservoir, belongs to the Nanpanjiang water system, in Yiliang County, Yunnan Province in March 2019, all of which were caught by using ground cages with a total of 15 fish. Parent fish were packed into plastic fry bags with a length of 80 cm and a width of 50 cm, which were flushed with oxygen and brought back to the breeding base.

4. Cultivation of Parent Fish

The parent fish collected in the field was placed in a sterilized cultivation cylinder, and a black PVC tube with a length of 30 cm and a diameter of 15 cm was placed in the cultivation cylinder; the water temperature was 16° C., water flow velocity was 20 cm/s, the concentration of dissolved oxygen of water was 6.0 mg/L, and water pH was 7.0. SRF1 feed was fed at 10:00 and 16:00 every day. After 1 week of domesticating, 2 parent fish died in total.

During the propagative period, neither female nor male parent fish had pearl stars, and there was no obvious roughness when touched by hand; in morphology, female parent fish abdomen was enlarged and round due to pregnancy, and eggs were flow out when the abdomen was lightly pressed.

5. Artificial Insemination

In the breeding period, the male and female parent fish with good gonad development and disease-free were selected for artificial inseminating. The eggs and sperm of the parent fish were gently squeezed into a pre-prepared container, and immediately stirred gently with chicken feathers for 30 s. Then, the sperm-egg mixture was rinsed gently with water with osmotic pressure of 280 mOsm/L and temperature of 20° C. After rinsing for 3 times, the sperm-egg mixture was evenly splashed on the sterilized and washed palmsheet.

6. Incubation Offish Eggs

The palmsheet adhered with fertilized eggs were placed in a sterilized and washed incubating pond (5 m×4 m×1.5 m) with a water level of 1.2 m, water surface 40 cm above the eggs, which was covered with shading net to ensure that there was no direct light source, the water temperature was 20° C., the water pH was 6.8 and the concentration of dissolved oxygen of water was 8.0 mg/L; every day, the eggs were sterilized in 100 ppm potassium permanganate solution for 20 min for 4 consecutive days. The fries incubated on the 5th day, and the incubation ended on the 8th day.

7. Breeding of Fries

The fries were fed 7 days after breaking egg membrane, and the water quality was regulated by adding nutrifying bacteria at 15 g/m$^2$ every day. Different feeds were fed according to stages, wherein, in the fry rearing stage:

from the 1st to 7th day of the feeding period, pulpous SRF4 was fed 4 times per day, and the feeding amount was 8 mL/m$^2$;

from the 8th to 20th day, the feed SCF5 and rotifer were fed 3 times per day, and the feeding amount of rotifer was 1.5 million/m$^2$, the feeding amount of feed SCF5 was 12 mL/m$^2$;

from the 21st to 60th day, the feed SCF6 was fed with the feeding amount of 10 g/m$^2$;

after 60 days of feeding, the fries were fed with feed used for parent fish culture, and the feeding amount was according to the feed coefficient of 3%, and the feeding amount was consumed within 15 min, the adult of S. rhinocerous was obtained after feeding for 1 year.

The sperm and eggs quality, fertilization rate, incubating rate, survival rate and deformity rate during the cultivation process of Examples 1 to 3 were respectively counted. The results are shown in Table 1.

TABLE 1

Summary of statistical index results of Examples 1-3

| Group | Egg Nucleus Deviation Rate | Sperm Motility | Fertilization Rate | Incubating Rate | Survival Rate | Deformity Rate | Survival Rate after 60 Days | Deformity Rate after 60 Days |
|---|---|---|---|---|---|---|---|---|
| Example 1 | 85% | 86% | 89% | 85% | 95% | 0.1% | 90% | 1.0% |
| Example 2 | 88% | 88% | 90% | 88% | 92% | 0.2% | 92% | 1.0% |
| Example 3 | 90% | 85% | 85% | 86% | 95% | 0.1% | 90% | 1.0% |

Comparative Example 1

1. Building a Breeding System

Parent fish cultivation cylinder was established, the specification of the cultivation cylinder was 1 m×0.8 m×1 m (length×width×height), and the cultivation container was kept dark throughout the year, and there was no noise around it, the parameters of water temperature, water flow intensity and water quality were controlled according to uniform parameters, i.e., the temperature was controlled at 18° C., the water flow rate was controlled at 15 cm/s, the concentration of dissolved oxygen of water was controlled at 6.5 mg/L, and the water pH was controlled at 7.0. The filtration device of the incubation container was cleaned every day to keep the water quality clean.

2. Preparation of Feed

SRF1 feed: mash feed containing 50% crude protein, earthworm, shrimp, vitamin D3 calcium tablets, multi-vitamin tablets and water; mash feed containing 50% crude protein: earthworm:shrimp:vitamin D3 calcium tablets:multi-vitamin tablets:water=250:100:20:10:8:300 (mass ratio).

3. Source of Parent Fish

The parent fish was collected in a cave next to the Chaishitan reservoir, belongs to the Nanpanjiang water system, in Yiliang County, Yunnan Province in May 2012, all of which were caught by using ground cages with a total of 12 fish. Parent fish were packed into plastic fry bags with a length of 80 cm and a width of 50 cm, which were flushed with oxygen and brought back to the breeding base.

4. Cultivation of Parent Fish

The parent fish collected in the field was placed in a sterilized cultivation cylinder, and a black PVC tube with a length of 30 cm and a diameter of 15 cm was placed in the cultivation cylinder; the water temperature was 18° C., water flow velocity was 15 cm/s, the concentration of dissolved oxygen of water was 6.5 mg/L, and water pH was 7.0. SRF1 feed was fed at 10:00 and 16:00 every day. After 1 week of domesticating, 5 parent fish died in total.

According to the above scheme, the growth status of $S.$ $rhinocerous$ was acceptable, but by April 2015, there were still no individuals with well-developed gonads capable of ovulation and fertilization.

Comparative Example 2

1. Building a Breeding System

It was the same as the aquaculture system in Example 1.

2. Preparation of Feed

The parent fish feed included: 111 carp brood fish feed, mash feed containing 30% crude protein, multi-vitamin tablets and water, 111 carp brood fish feed: mash feed containing 30% crude protein:multi-vitamin tablets:water=100:150:50:300 (mass ratio).

The pulpous feed included: boiled egg yolk, shrimp, multi-vitamin tablets and water, boiled egg yolk: shrimp:multi-vitamin tablets:water=200:200:20:750 (mass ratio).

3. Source of Parent Fish

The parent fish was collected in a cave next to the Chaishitan reservoir, belongs to the Nanpanjiang water system, in Yiliang County, Yunnan Province in February 2015, all of which were caught by using ground cages with a total of 13 fish. Parent fish were packed into plastic fry bags with a length of 80 cm and a width of 50 cm, which were flushed with oxygen and brought back to the breeding base.

4. Domestication of Parent Fish

The parent fish collected in the field was placed in a sterilized cultivation cylinder, and a black PVC tube with a length of 30 cm and a diameter of 15 cm was placed in the cultivation cylinder; the water temperature was 16° C., water flow velocity was 20 cm/s, the concentration of dissolved oxygen of water was 6.0 mg/L, and water pH was 7.0. SRF1 feed was fed at 10:00 and 16:00 every day. After 1 week of domesticating, 3 parent fish died in total.

During the propagative period, neither female nor male parent fish had pearl stars, and there was no obvious roughness when touched by hand; in morphology, female parent fish abdomen was enlarged and round due to pregnancy, and eggs were flow out when the abdomen was lightly pressed.

5. Artificial Insemination

In the breeding period, the male and female parent fish with good gonad development and disease-free were selected for artificial inseminating. The eggs and sperm of the parent fish were gently squeezed into a pre-prepared container, and immediately stirred gently with chicken feathers for 30 s. Then, the sperm-egg mixture was rinsed gently with water with osmotic pressure of 280 mOsm/L and temperature of 20° C. After rinsing for 3 times, the sperm-egg mixture was evenly splashed on the sterilized and washed palmsheet.

6. Incubation of Fish Eggs

The palmsheet adhered with fertilized eggs were placed in a sterilized and washed incubating pond (5 m×4 m×1.5 m) with a water level of 1.2 m, water surface 40 cm above the eggs, which was covered with shading net to ensure that there was no direct light source, the water temperature was 20° C., the water pH was 6.8 and the concentration of dissolved oxygen of water was 8.0 mg/L; every day, the eggs were sterilized in 100 ppm potassium permanganate solution for 20 min for 4 consecutive days. The fries incubated on the 5th day, and the incubation ended on the 8th day.

7. Breeding of Fries

The fries were fed 7 days after breaking egg membrane, and the water quality was regulated by adding nutrifying bacteria at 15 g/m² every day. The pulpous feed was fed during the feeding period, after 60 days of feeding, the fries were fed with feed used for parent fish culture, and the feeding amount was according to the feed coefficient of 3%, the feeding amount was consumed within 15 min.

The sperm and eggs quality, fertilization rate, incubating rate, survival rate and deformity rate during the cultivation process of Comparative Examples 1 to 2 were respectively counted. The results are shown in Table 2.

TABLE 2

Summary of statistical index results of Comparative Examples 1-2

| Group | Egg Nucleus Deviation Rate | Sperm Motility | Fertilization Rate | Incubating Rate | Survival Rate | Deformity Rate | Survival Rate after 60 Days | Deformity Rate after 60 Days |
|---|---|---|---|---|---|---|---|---|
| Comparative Example 1 | Unsqueezed egg | Unsqueezed egg | — | — | — | — | — | — |
| Comparative Example 2 | 70% | 75% | 78% | 60% | 40% | 30% | 30% | 32% |

The above described are only preferred embodiments of the present disclosure, it should be understood by those skilled in the art that, without departing from the principle of the present application, any improvements and modifications fall into the scope of the present disclosure.

What is claimed is:

1. An artificial propagation method of *Sinocyclocheilus rhinocerous*, comprising the following steps:
   placing female and male parent fish in a sterilized culture container for parent fish culture, wherein black cave simulant is placed in the culture container in advance; environmental parameters during the parent fish culture are as follows: water temperature is in a range of 16-20° C., water flow velocity is in a range of 5-20 cm/s, concentration of dissolved oxygen of water is in a range of 6.0-7.0 mg/L, and water pH is in a range of 6.8-7.2, keeping the water clean; keeping a culture environment dark and noiseless;
   during the parent fish culture, feeding pellet feed twice a day, and feeding amount is according to feed coefficient of 3%-4%, the pellet feed is a mixture of mash feed containing 40%-50% crude protein, earthworm, shrimp, vitamin D3 calcium tablets, multi-vitamin tablets and water, with a mass ratio of 250-280:80-100: 10-20:10-20:8-20:300;
   collecting sperm and eggs for artificial inseminating after gonads of female and male parent fish mature, rinsing sperm-egg mixture with normal saline with osmotic pressure of 280-320 mOsm/L and temperature of 18-20° C. for 3-4 times, then splashing the sperm-egg mixture on a sterilized palm sheet, and incubating the palm sheet adhered with fertilized eggs in an incubating pond for 7-8 days, breeding incubating fries to obtain adult fish of *Sinocyclocheilus rhinocerous*.

2. The artificial propagation method of *Sinocyclocheilus rhinocerous* according to claim 1, wherein the environmental parameters of parent fish culture are rhythmically regulated:
   in Stage 1, for 4 months, the water temperature is in the range of 16-20° C., the water flow velocity is in the range of 10-20 cm/s, the concentration of dissolved oxygen of water is in the range of 6.0-7.0 mg/L, and the water pH is in the range of 6.8-7.0;
   in Stage 2, for 4 months, the water temperature is in the range of 18-20° C., the water flow velocity is in the range of 5-15 cm/s, the concentration of dissolved oxygen of water is in the range of 6.0-6.5 mg/L, and the water pH is in the range of 6.8-7.2;
   in Stage 3, for 4 months, the water temperature is in the range of 16-18° C., the water flow velocity is in the range of 5-15 cm/s, the concentration of dissolved oxygen of water is in the range of 6.0-7.0 mg/L, and the water pH is in the range of 6.8-7.2.

3. The artificial propagation method of *Sinocyclocheilus rhinocerous* according to claim 1, wherein a type of pellet feed is rhythmically regulated according to cultivation month:
   feeding feed SRF1 in Stage 1, wherein the feed SRF1 is a mixture of mash feed containing 50% crude protein, earthworm, shrimp, vitamin D3 calcium tablets, multi-vitamin tablets and water, with a mass ratio of 250: 100:20:10:8:300;
   feeding feed SRF2 in Stage 2, wherein the feed SRF2 is a mixture of mash feed containing 40% crude protein, earthworm, shrimp, vitamin D3 calcium tablets, multi-vitamin tablets and water, with a mass ratio of 280:80: 10:20:10:300;
   feeding feed SRF3 in Stage 3, wherein the feed SRF3 is a mixture of mash feed containing 45% crude protein, earthworm, shrimp, vitamin D3 calcium tablets, multi-vitamin tablets and water, with a mass ratio of 250: 100:10:20:20:300.

4. The artificial propagation method of *Sinocyclocheilus rhinocerous* according to claim 1, wherein environmental conditions for incubation are as follows:
   water level is 1.2 m, water surface is in a range of 40-80 cm above fish eggs, no direct light source, the water temperature is in the range of 18-20° C., the water pH is in the range of 6.8-7.5, the concentration of dissolved oxygen of water is in the range of 7.0-8.0 mg/L.

5. The artificial propagation method of *Sinocyclocheilus rhinocerous* according to claim 4, wherein the fertilized eggs are sterilized during incubating;
   sterilizing comprising: sterilizing the fertilized eggs in 80-120 ppm potassium permanganate solution for 15-25 min, and sterilizing for four consecutive days.

6. The artificial propagation method of *Sinocyclocheilus rhinocerous* according to claim 1, wherein water quality is regulated by adding nitrifying bacteria in an amount of 15-17 g/m$^2$ every day during a feeding period.

7. The artificial propagation method of *Sinocyclocheilus rhinocerous* according to claim 6, wherein the fries are fed seven days after breaking egg membrane, and the feed is fed in stages during the feeding period.

8. The artificial propagation method of *Sinocyclocheilus rhinocerous* according to claim 7, wherein feeding pulpous feed SRF4 from the first day to the seventh day of feeding, four times per day with the feeding amount of 8-10 mL/m$^2$, the pulpous feed SRF4 is a mixture of boiled egg yolk, earthworm, shrimp, multi-vitamin tablets and water, with a mass ratio of 300:20:20:10:750;
   feeding feed SRF5 and rotifer from the eighth day to the twentieth day of feeding, three times per day, the feeding amount of feed SRF5 each time is 10-15 mL/m$^2$; the feeding amount of rotifer each time is 1.5 million/m$^2$, wherein the feed SRF5 is a mixture of boiled egg yolk, earthworm, shrimp, freshly ground soybean milk, multi-vitamin tablets and water, with a mass ratio of 250:20:20:250:10:750;
   feeding feed SRF6 from the twenty-first day to the sixtieth day of feeding, twice a day with the feeding amount of 10-12 g/m$^2$, wherein the feed SRF6 is a mixture of freshly ground soybean milk, earthworm, shrimp, mash feed containing 40% crude protein, vitamin D3 calcium tablets, multi-vitamin tablets and water, with a mass ratio of 250:10:10:250:10:10:750;
   after feeding for sixty days, feeding pellet feed twice a day, the feeding amount each time is according to the feed coefficient of 3%-4%.

9. The artificial propagation method of *Sinocyclocheilus rhinocerous* according to claim 2, wherein environmental conditions for incubation are as follows:
   water level is 1.2 m, water surface is in a range of 40-80 cm above fish eggs, no direct light source, the water temperature is in the range of 18-20° C., the water pH is in the range of 6.8-7.5, the concentration of dissolved oxygen of water is in the range of 7.0-8.0 mg/L.

10. The artificial propagation method of *Sinocyclocheilus rhinocerous* according to claim 3, wherein environmental conditions for incubation are as follows:
    water level is 1.2 m, water surface is in a range of 40-80 cm above fish eggs, no direct light source, the water temperature is in the range of 18-20° C., the water pH is in the range of 6.8-7.5, the concentration of dissolved oxygen of water is in the range of 7.0-8.0 mg/L.

11. The artificial propagation method of *Sinocyclocheilus rhinocerous* according to claim 9, wherein the fertilized eggs are sterilized during incubating;
   sterilizing comprising: sterilizing the fertilized eggs in 80-120 ppm potassium permanganate solution for 15-25 min, and sterilizing for four consecutive days.

12. The artificial propagation method of *Sinocyclocheilus rhinocerous* according to claim 10, wherein the fertilized eggs are sterilized during incubating;
   sterilizing comprising: sterilizing the fertilized eggs in 80-120 ppm potassium permanganate solution for 15-25 min, and sterilizing for four consecutive days.

13. The artificial propagation method of *Sinocyclocheilus rhinocerous* according to claim 2, wherein water quality is regulated by adding nitrifying bacteria in an amount of 15-17 g/m$^2$ every day during a feeding period.

14. The artificial propagation method of *Sinocyclocheilus rhinocerous* according to claim 3, wherein water quality is regulated by adding nitrifying bacteria in an amount of 15-17 g/m$^2$ every day during a feeding period.

15. The artificial propagation method of *Sinocyclocheilus rhinocerous* according to claim 13, wherein the fries are fed seven days after breaking egg membrane, and the feed is fed in stages during the feeding period.

16. The artificial propagation method of *Sinocyclocheilus rhinocerous* according to claim 14, wherein the fries are fed seven days after breaking egg membrane, and the feed is fed in stages during the feeding period.

17. The artificial propagation method of *Sinocyclocheilus rhinoceros* according to claim 15, wherein feeding pulpous feed SRF4 from the first day to the seventh day of feeding, four times per day with the feeding amount of 8-10 mL/m$^2$, the pulpous feed SRF4 is a mixture of boiled egg yolk, earthworm, shrimp, multi-vitamin tablets and water, with a mass ratio of 300:20:20:10:750;
   feeding feed SRF5 and rotifer from the eighth day to the twentieth day of feeding, three times per day, the feeding amount of feed SRF5 each time is 10-15 mL/m$^2$; the feeding amount of rotifer each time is 1.5 million/m$^2$, wherein the feed SRF5 is a mixture of boiled egg yolk, earthworm, shrimp, freshly ground soybean milk, multi-vitamin tablets and water, with a mass ratio of 250:20:20:250:10:750;
   feeding feed SRF6 from the twenty-first day to the sixtieth day of feeding, twice a day with the feeding amount of 10-12 g/m$^2$, wherein the feed SRF6 is a mixture of freshly ground soybean milk, earthworm, shrimp, mash feed containing 40% crude protein, vitamin D3 calcium tablets, multi-vitamin tablets and water, with a mass ratio of 250:10:10:250:10:10:750;
   after feeding for sixty days, feeding pellet feed twice a day, the feeding amount each time is according to the feed coefficient of 3%- 4%.

18. The artificial propagation method of *Sinocyclocheilus rhinocerous* according to claim 16, wherein feeding pulpous feed SRF4 from the first day to the seventh day of feeding, four times per day with the feeding amount of 8-10 mL/m$^2$, the pulpous feed SRF4 is a mixture of boiled egg yolk, earthworm, shrimp, multi-vitamin tablets and water, with a mass ratio of 300:20:20:10:750;
   feeding feed SRF5 and rotifer from the eighth day to the twentieth day of feeding, three times per day, the feeding amount of feed SRF5 each time is 10-15 mL/m$^2$; the feeding amount of rotifer each time is 1.5 million/m$^2$, wherein the feed SRF5 is a mixture of boiled egg yolk, earthworm, shrimp, freshly ground soybean milk, multi-vitamin tablets and water, with a mass ratio of 250:20:20:250:10:750;
   feeding feed SRF6 from the twenty-first day to the sixtieth day of feeding, twice a day with the feeding amount of 10-12 g/m$^2$, wherein the feed SRF6 is a mixture of freshly ground soybean milk, earthworm, shrimp, mash feed containing 40% crude protein, vitamin D3 calcium tablets, multi-vitamin tablets and water, with a mass ratio of 250:10:10:250:10:10:750;
   after feeding for sixty days, feeding pellet feed twice a day, the feeding amount each time is according to the feed coefficient of 3%- 4%.

\* \* \* \* \*